(12) United States Patent
Lammers et al.

(10) Patent No.: US 6,308,706 B1
(45) Date of Patent: Oct. 30, 2001

(54) DEVICE AND PROCESS FOR MONITORING THE RESPIRATION PARAMETERS OF AN ARTIFICIAL RESPIRATION SYSTEM

(76) Inventors: Léon Lammers, Bandholm 142, NL-2133 DN Hoofddorp (NL); Karl Siegfried Cornelius-Lorenz, Stegemühlenweg 37, D-37083 Göttingen; Klaus Züchner, Angerstrasse 12a, D-37073 Göttingen, both of (DE)

( * ) Notice: Subject to any disclaimer, the term of this patent is extended or adjusted under 35 U.S.C. 154(b) by 0 days.

(21) Appl. No.: 09/142,437
(22) PCT Filed: Mar. 7, 1997
(86) PCT No.: PCT/DE97/00444
§ 371 Date: Jan. 22, 1999
§ 102(e) Date: Jan. 22, 1999
(87) PCT Pub. No.: WO97/32619
PCT Pub. Date: Sep. 12, 1997

(30) Foreign Application Priority Data

Mar. 8, 1996 (NL) .................................................... 607/96

(51) Int. Cl.$^7$ ................................................. A61M 16/00
(52) U.S. Cl. ............................. 128/204.22; 128/201.13; 128/205.29
(58) Field of Search ................ 128/204.18, 204.21, 128/204.22, 200.24, 201.13, 202.22, 204.17, 205.79, 207.14, 920, 923; 165/119; 342/396

(56) References Cited

U.S. PATENT DOCUMENTS 4,581,012  4/1986  Brown et al. .
5,549,106 * 8/1996  Gruenke et al. ................. 128/204.21
5,878,744 * 3/1999  Pfeiffer ............................. 128/204.22
5,915,381 * 6/1999  Nord ................................. 128/204.21

FOREIGN PATENT DOCUMENTS 0 627 196   12/1994  (EP) .
2 304 359   10/1976  (FR) .
2 505 658   11/1982  (FR) .

OTHER PUBLICATIONS

"Elastische Blende als Atemstromrezeptor"; University Fridericiana Karlsruhe, Germany; (Technical University) Dissertation of Manfred Frentzki, Halle/S. on Jul. 2, 1975.
Wm. W. Muschin et al: "Automatic Ventilation of the Lungs"; 1980; Blackwell Scientific Publications, pp. 178 to 183.

* cited by examiner

Primary Examiner—Glenn K. Dawson
(74) Attorney, Agent, or Firm—Collard & Roe, PC.

(57) ABSTRACT

A device is disclosed for monitoring the respiration parameters of an artificial respiration system. The proposed device has a treatment device including a filter and/or heat-and moisture exchanger fitted in a respiration tube system and is based on evaluation by a monitoring unit of pressure and/or flow-rate values in the respiration system. Inside the respiration system, pressure sensors are provided upstream and downstream of a flow resistance in the treatment device and pressure sensors are provided upstream and downstream of another flow resistance suitable as a reference. The signals from the pressure sensors are fed to the monitoring unit which determines the respiration parameters from the pressure difference $\Delta p_3$ above the flow resistance in the treatment device, the pressure difference $\Delta p_4$ above the other flow resistance suitable as a reference within the respiration system, and from the time t.

15 Claims, 5 Drawing Sheets

Figure 1:
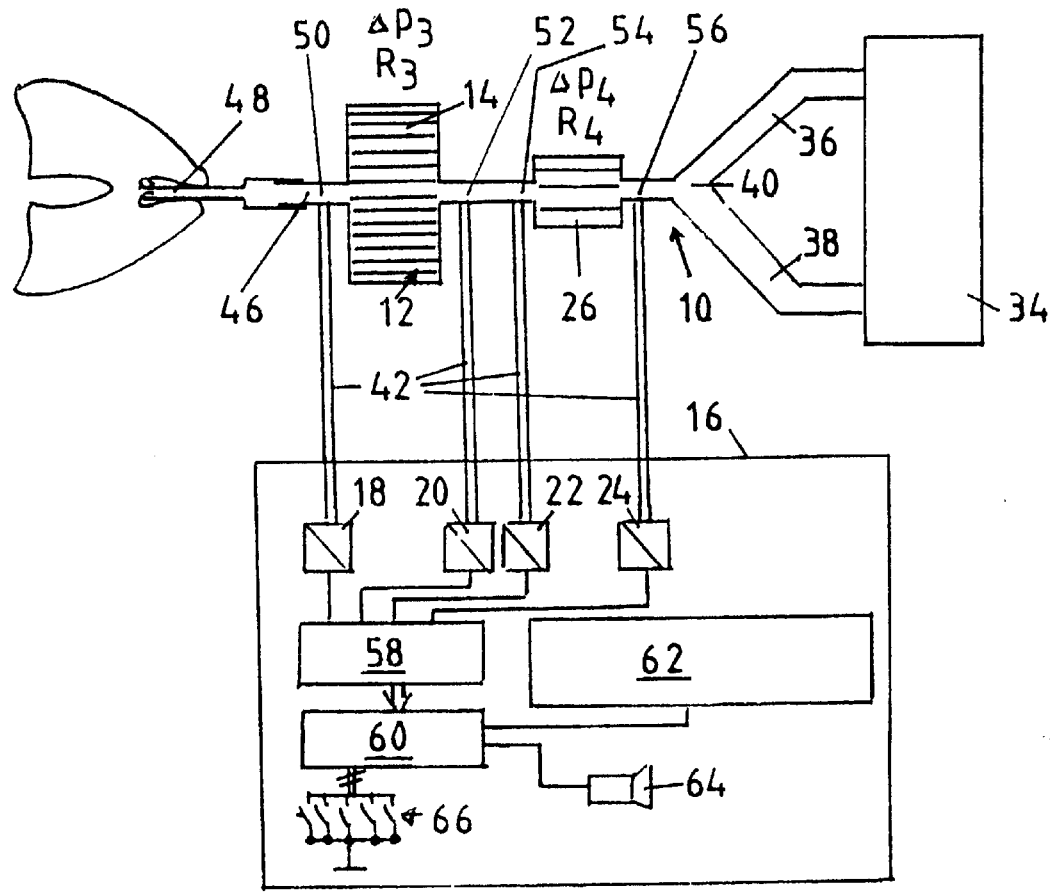

DEVICE AND PROCESS FOR MONITORING THE RESPIRATION PARAMETERS OF AN ARTIFICIAL RESPIRATION SYSTEM

The invention concerns a device and a process to monitor characteristic respiration values for a ventilation system 16 or 17.

In ventilation systems for artificial respiration of patients, it is very important to maintain heat and moisture values that largely correspond to the natural environment. Respiratory gases are usually supplied from canisters or a central supply system in which the respiratory gases are almost completely dry. This would dry out the air passages of the ventilated patient if countermeasures are not taken.

To maintain physiologically suitable heat and moisture values, prior-art heat and moisture exchangers (termed HEM) serving as treatment devices are placed in the ventilation tubing system. These absorb heat and moisture from the expired air and add them to the inspired air. The treatment device can also serve or be designed as a filter that keeps potential impurities out of the ventilation system and prevents the patient's germs from contaminating the ventilation system upon exhalation. If the flow resistance increases too much from excess impurities, the patient is forced to alter his breathing. In addition, there is the danger that the patient will not be supplied with sufficient respiratory gases. This undesirably burdens the patient. The caregivers must hence regularly check the breathing resistance in such treatment devices to avoid incidents.

In the generic French patent No. 23 04 359, there is a prior-art device to monitor characteristic respiratory values of a ventilation system with a heat and moisture exchanger. The flow resistance of the heat and moisture exchanger is used to determine the volumetric flow by pressure sensors before and after the flow resistance. In this reference, the problem is also discussed that the flow resistance of the heat and moisture exchanger changes in relation to the absorbed moisture. This change falsifies the calculation of the volumetric flow across the differential pressure of the flow resistance. To solve this problem, a change in the flow resistance is avoided. A drain is located under the heat and moisture exchanger that can remove the condensed moisture. Although in certain circumstance the change from condensed moisture from respirated air is reduced, the described measure is not able to avoid changes in the flow resistance when the heat and moisture exchanger become plugged from viscous sputum.

The invention is based on the problem of automatically detecting the characteristic breathing values with a high degree of precision and reliability using a device and process to monitor characteristic respiratory values without impairing the functioning of the respiratory system.

Using a device according to the preamble of claim 16 and a process according to the preamble of claim 17, this problem is solved by the features in the respective characteristics.

Developments and advantageous embodiments of the invention can be found in the subclaims.

Based on the relationship: of the flow resistance R equal to the differential pressure $\Delta p$ over volumetric flow V, and the relationship: of the volumetric flow V equal to volume V over time, one of the quantities can be calculated when the others are known. To obtain the flow resistance of the treatment device, the differential pressure across the treatment device and the volumetric flow must be known. The differential pressure is determined by pressure sensors before and after the treatment device. To also determine the flow resistance, another flow resistance is used as a suitable reference. Since it is also located in the ventilation system, the same volumetric flow flows through it. The volumetric flow can hence be calcuated from the differential pressure over the flow resistance serving as a reference, and the value of the reference flow resistance itself.

Accordingly, the value of the flow resistance of the treatment device can be continuously monitored, changes can be immediately determined, and an alarm can be given when a threshold is exceeded. Any other characteristic breathing value and resulting warning can be determined from the measured values by corresponding mathematical calculations. Hence caregivers only need to monitor the monitoring unit and not the ventilation system; in particular, the treatment device does not need to be monitored continuously.

The pressure sensors can detect pressure in the ventilation system with reference to the environment, or they can detect differential pressure via flow resistance. Pressure sensors that detect the pressure in reference to the environment can also detect the air passage pressure in the ventilation system. However, measuring is less complicated with pressure sensors that only detect differential pressure.

The flow resistance suitable as a reference within the ventilation system can be designed as a section of the ventilation tube system, as a diaphragm, or as a filter. When a section of the ventilation tubing system is incorporated as a reference, no additional flow resistance is necessary. However, the value of this flow resistance can easily vary when the ventilation tubing system is displaced. The other option of using a diaphragm concentrates the reference flow resistance within a short path, but the flow is largely nonlinear, and this requires special compensation. A filter has proven to be the best reference flow resistance. A filter combines the advantage of a concentrated arrangement with the advantage of linear behavior at different flow speeds.

A particularly suitable reference filter is designed as fleece which is economical to manufacture and can be reproduced with a high degree of precision.

The fleece preferably extends over a cross-section that is substantially greater than the cross-section of the ventilation tubing. The flow rate is lower than that of the ventilation tubing which prevents swirling and nonlinear flow characteristics. In addition, there is a greater capture area for impurities so that the flow resistance remains largely constant.

In one advantageous embodiment, the filter is integrated into the housing of the treatment device. This measure limits the number of potentially faulty plug connections as well as the length and weight of the ventilation device, and there is less dead space in the ventilation system to reduce undesirable reinhalation of exhaled gases.

Connecting channels for the pressure sensors preferably terminate in areas of the treatment device and the flow resistance suitable as a reference in the ventilation system in which comparatively low flow speeds predominate. A change in the pressure and hence falsification of the measured values by the Venturi effect is avoided.

In one development, the connecting channels for the pressure sensors in the housing of the treatment device lead to a common connection arrangement. This protects the connecting channels that can be compactly connected to the pressure sensors from the connection arrangement.

Furthermore, the ventilation tubing system between the treatment device and ventilation device can be divided into a separate inhalation tube and exhalation tube that are joined directly before the treatment device.

A particularly advantageous ventilation tubing system has coaxial inhalation and exhalation tubes between the treatment device and ventilation device. This exploits the advantage of separate tubes without having two external tubes. In addition, this embodiment allows the exchange of heat.

In another development, a single or common plug connection is created for the connection of the junction of the inhalation tube and the exhalation tube to the treatment device, and the connection of the tubes joined with the pressure sensors to the connection arrangement in the treatment device. The tubes connected to the pressure sensors can run along the ventilation tubing system or integrated in it. This substantially reduces the time spent for setting up and taking apart the ventilation system. The common connection is also more reliable and sturdy than several separate connections at different locations. In addition, the number of unmonitored tubes and cables that can hence disturb the treatment process are reduced.

As needed, numerous characteristic quantities can be derived from the measured values such as flow resistance of the treatment device, tidal volume, respiratory minute volume, breathing frequency, tube blockage, air trapping e.g. for asthmatics, air passage pressure or density of the respiratory system. It is therefore not necessary to use separate meters and measuring sensors with the corresponding cables and tubes.

In the following, the invention will be further explained with reference to an exemplary embodiment that is represented in the drawings.

Figure 2:
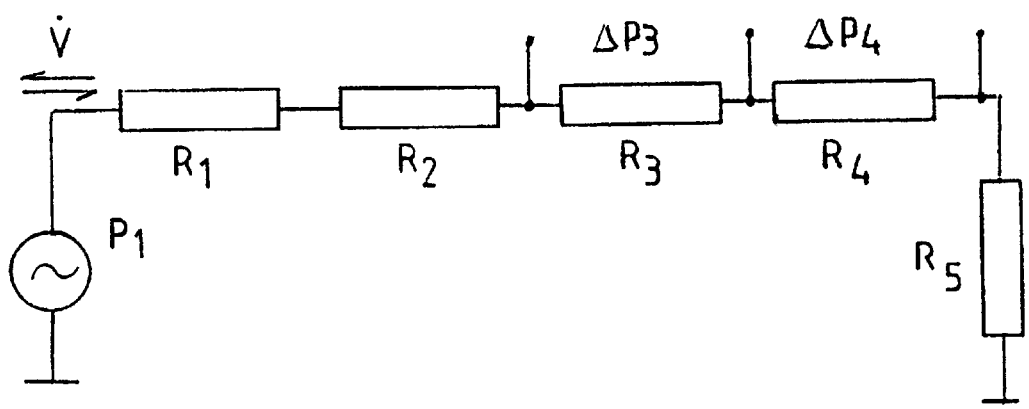
Figure 3:
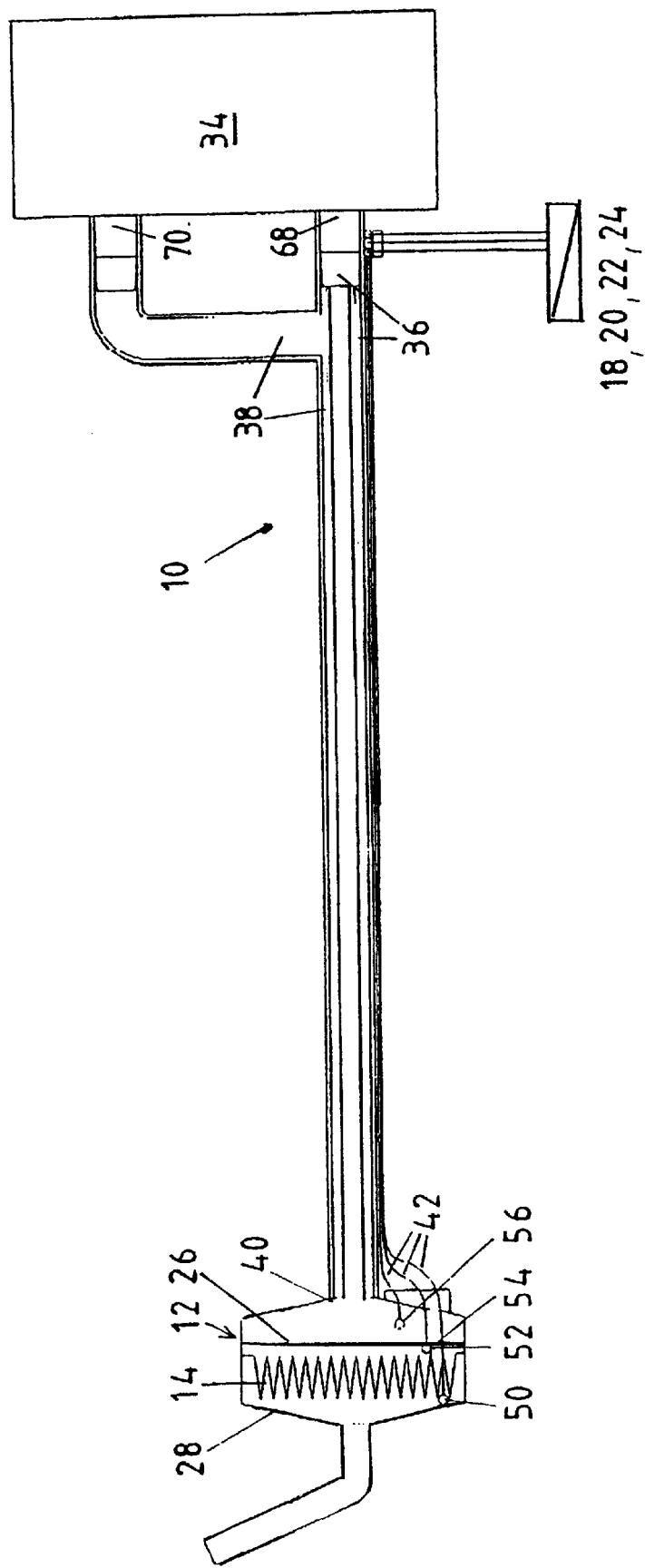
Figure 4:
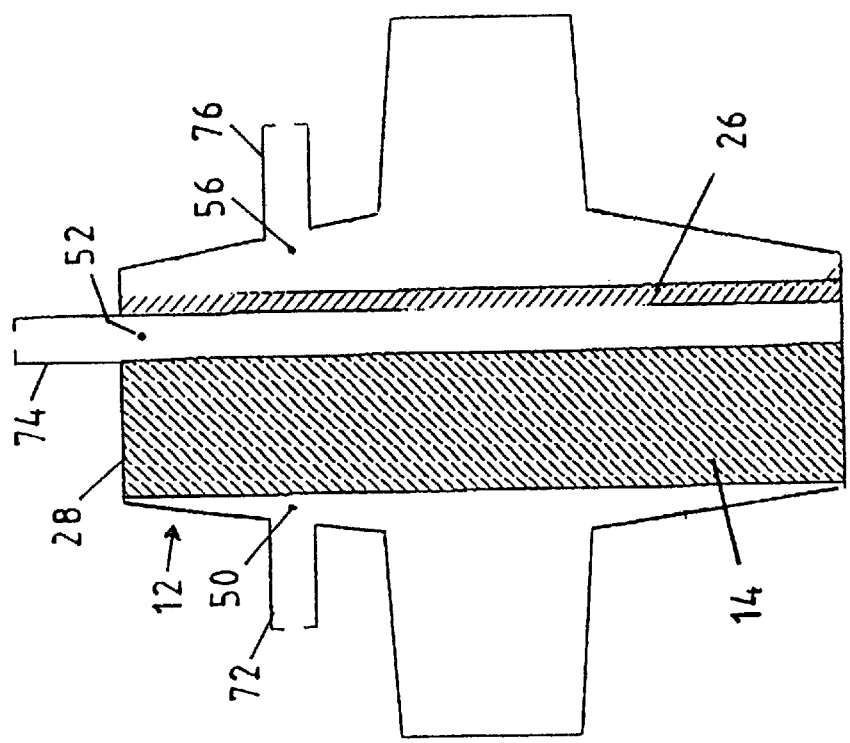
Figure 5:
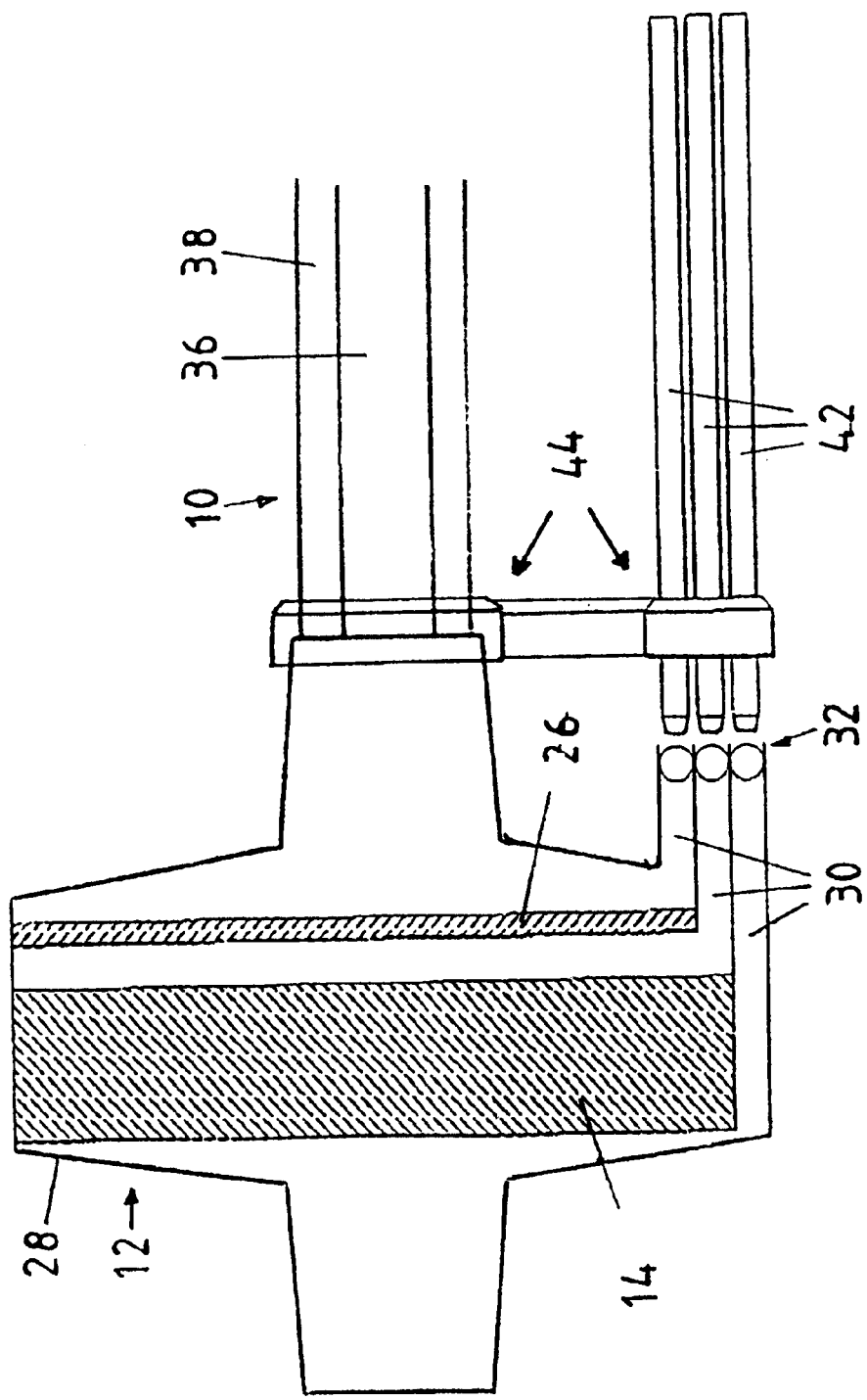
Figure 6:
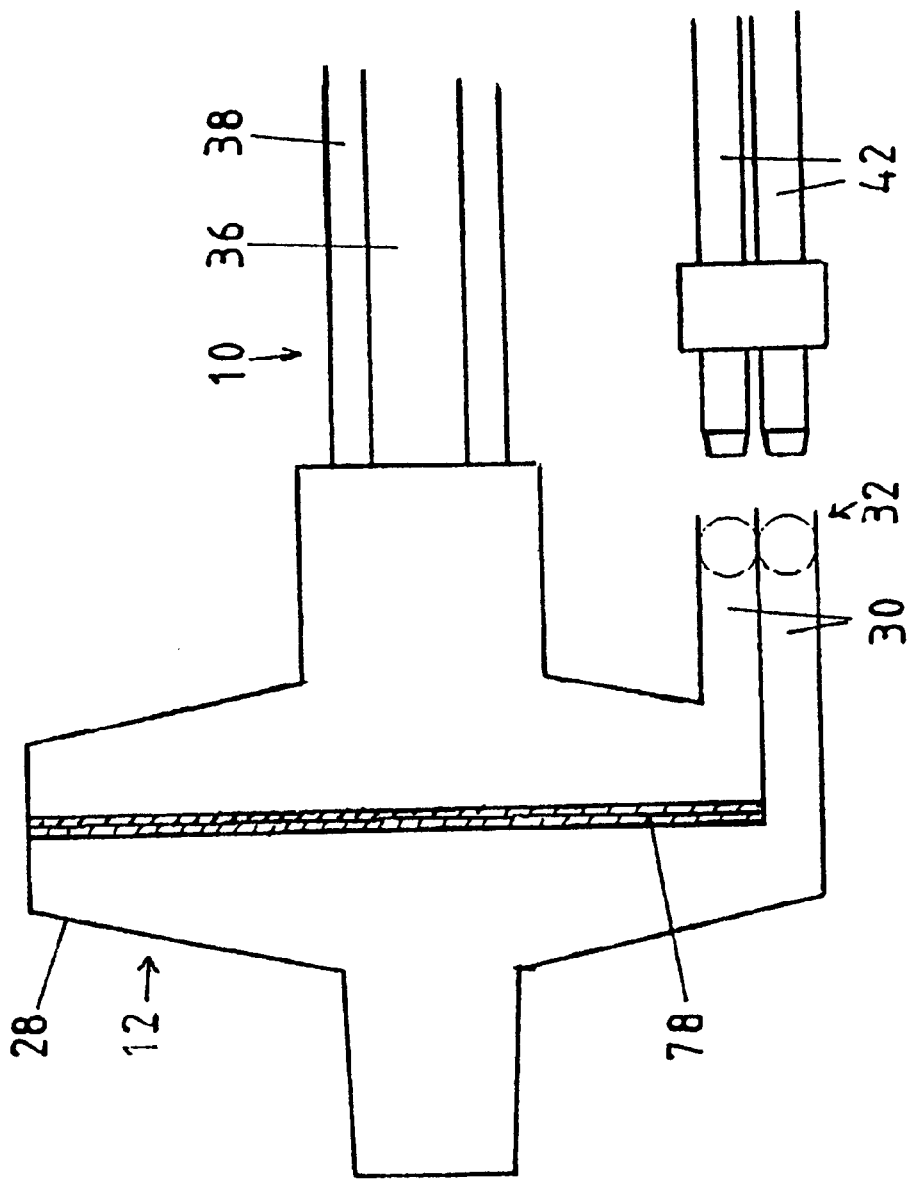

The drawings show the following:

FIG. 1 A schematic representation of a ventilation system,

FIG. 2 An equivalent circuit diagram of the ventilation system,

FIG. 3 A lengthwise ventilation tubing system and a treatment device with an integrated reference filter, FIG. 4 A first embodiment of a lengthwise section of a treatment device with an integrated reference filter, FIG. 5 A second embodiment of a lengthwise section of a treatment device with an integrated reference filter, and FIG. 6 A lengthwise section of a treatment device with just one filter.

The schematic representation in FIG. 1 of a ventilation system comprises a ventilator 34 to which the ventilation tubing system 10 with a treatment device 12 is connected, a tube 46 that is intubated in the trachea 48 of a patient, pressure sensors 18, 20, 22, 24 and a monitor 16. The treatment device 12 can contain a heat and moisture exchanger 14. The heat and moisture exchanger 14 can simultaneously be designed as a filter. Alternately, it is also possible for the treatment device 12 to have only one filter. This depends on whether there already is an independent moisturizing and heating device. In addition, the ventilation system comprises an additional flow resistor $R_4$ that serves as a reference which is used as an additional filter 26 in the ventilation tubing system 10.

The ventilation tubing system 10 consists of an inhalation tube 36 and an exhalation tube 38 that are joined before the treatment device 12 with a junction 40.

Thin measuring tubes 42 from measuring points 50, 52 before and after the treatment device 12 and measuring sites 54, 56 before and after the reference filter 26 run to the pressure sensors 18, 20, 22, 24 that are installed in the monitor. The pressure sensors 18, 20, 22, 24 detect the pressure in reference to the atmospheric pressure. It is also possible to use pressure sensors that only measure the difference across the treatment device 12 and across the reference filter 26. The outputs for the pressure sensors 18, 20, 22, 24 are connected to a central processor 60 (possibly via an A/D converter 58) of the monitor 16. A display 62, an alarm generator 64 and operating keys 66 or a keypad are connected to the central processor 60. In addition, an electronic memory and/or a printer can be connected.

FIG. 2 shows an equivalent circuit diagram of the ventilation system from FIG. 1. The breathing activity of a patient's lungs is represented as pressure source $P_1$ that is series-connected to the resistance $R_1$ of the air passage 48, the resistance $R_2$ of the tube 46, the resistance $R_3$ of the treatment device, resistance $R_4$ of reference filter 26, and the resistance $R_5$ of the ventilation tubing system 10 and ventilator 34. A volumetric flow V (indicated by arrows) is created from the respiratory activity. A differential pressure $\Delta p_3$ is detected across resistance $R_3$, and another differential pressure $Rp_4$ of the reference filter 26 is detected across resistance $R_4$. The volumetric flow V is then $V=R_4/\Delta p_4$. The flow resistance $R_3$ of the treatment device 12 is $R_3=\Delta p_3/V$. The volume V of the air inhaled by the patient is calculated as $V=\int V_{insp}$ dt from the inspirated volumetric flow $V_{insp}$. The same holds true for the volume of expired air. All relevant characteristic respiratory values and their changes can hence be easily calculated. By comparing them with thresholds, it is also possible to immediately detect and signal states that are critical for the patient.

FIG. 3 shows a lengthwise section of a ventilation tubing system 10 and a treatment device 12. The ventilation tubing system 10 consists of an inspiration tube 36 and an expiration tube 38 and a junction 40. The inhalation tube 36 is coaxial inside the exhalation tube 38. Connections 68, 70 of the inhalation tube 36 and the expiration tube 38 are connected to a ventilator 34. The treatment device 12 is connected to the junction 40 of the inhalation tube 36 and the exhalation tube 38. Measuring tubes 42 that lead from measuring points 50, 52, 54, 56 to the pressure sensors 18, 20, 22, 24 can be parallel to the ventilation tubing system 10 or integrated in it. The treatment device 12 comprises a heat and moisture exchanger 14 and a reference filter 26 that is directly next to the heat and moisture exchanger 14 in the same housing 28. In this design, a common measuring site 52 between the heat and moisture exchanger 14 and the reference filter 26 is sufficient to measure the pressure before and after the heat and moisture exchanger 14 and before and after the reference filter 26. Likewise, the pressure sensors 20 and 22 can be replaced by a single pressure sensor.

FIG. 4 and 5 show different embodiments of the heat and moisture exchanger 14 with the integrated reference filter 26. In FIG. 4, the measuring points 50, 52, 56 are on the outer edge of the housing 28 that is larger than the ventilation tubing system 10 (shown in a cross-section). The flow speeds of the respiration gases at these sites are low in comparison to the flow speed in the ventilation tubing system 10. The measured values are hence not influenced by the Venturi effect. In the embodiment in FIG. 4, the connections 72, 74, 76 are directly adjacent to the measuring sites 50, 52, 56 on the housing.

In contrast, FIG. 5 shows an embodiment where the connection channels 30 are guided in the housing 28 of the treatment device 12 to a common connection system 32. This connection system 32 is on the same side of the housing 28 at which the ventilation tubing system 10 is connected. The connection system 32 for the measuring tubes 42 and the connection of the ventilation tubing system 10 is designed in this instance as a common plug connection 44. No parts therefore extend beyond the outer edge of the housing 28 of the treatment device 12 which protects the connection unit 32. In addition, the measuring tube 42 is parallel to the ventilation tubing system 10 and can be integrated into the system without bending or curving it.

Alternately, FIG. 6 shows an embodiment where the treatment device 12 is only a filter 78 that can be designed similar or identical to the reference filter 26. If the ventilation device 34 is used to adapt the heat and moisture, the heat and moisture exchanger used with the other embodiments can be dispensed with. Otherwise, the embodiment corresponds to that in FIG. 5. With the exception of a plugged filter 78 and the related quantities, all other characteristic respiration quantities can be calculated with a high degree of precision. This design can hence replace prior art solutions that use diaphragms, resistance lines or Venturi tubes, and the flow rates during respiration and spontaneous breathing are also highly linear.

In the following, two situations will be clarified in which the detected characteristic respiration values indicate alarm states. 1. The tidal volume can be determined by measuring the differential pressure $\Delta p_4$ across the reference filter 26 and integrating it over time t. If the integral is too low, the tidal volume is also too low which represents an alarm state. This can be indicated by a visual or acoustic signal that provides a notice for immediate intervention. 2. The heat and moisture exchanger 14 is gradually plugged by mucous which increases its resistance $R_1$ and hence the differential pressure $\Delta p_1$ measured across it. To differentiate this pressure rise from an increase in pressure from a higher volumetric flow, the differential pressure $\Delta p_4$ of the reference filter 26 is also evaluated. Comparing the differential pressures can then provide a clear indication of whether the pressure rise is from the heat and moisture exchanger 14 being plugged or from an increase in the volumetric flow, and an alarm can be triggered if necessary.

What is claimed is:

1. A ventilation system comprising
   (a) a ventilation tube system comprising a treatment device for creating a first flow resistance and a device selected from the group consisting of a filter and a heat and moisture exchanger;
   (b) a monitoring unit for evaluating ventilation system quantities selected from the group consisting of pressure quantities and flow quantities;
   (c) first and second pressure sensors located respectively upstream and downstream of the treatment device;
   (d) means for creating a second flow resistance in series to the first flow resistance, said second flow resistance being suitable as a reference;
   (e) third and fourth pressure sensors located respectively upstream and downstream of the means for creating a second flow resistance;
   (f) whereby said pressure sensors feed signals to the monitoring unit, the monitoring unit calculating selected parameters derived from a first differential pressure across the first flow resistance and a second differential pressure across the second flow resistance as a function of time to determine the degree of permeability of the filter or exchanger.

2. The system according to claim 1 whereby the pressure sensors determine the pressures in the ventilation system in reference to the environmental pressure, or detect differential pressures across the flow resistances.

3. The system according to claim 1 whereby a flow resistance suitable as a reference inside the ventilation system is designed as a section of the ventilation tube system, or as a diaphragm or a reference filter.

4. The system according to claim 3 whereby the reference filter is designed as a fleece.

5. The system according to claim 4 whereby the fleece extends across a substantially larger cross-section in comparison to the cross-section of the ventilation tube system.

6. The system according to claim 3 whereby the treatment device comprises a housing and the reference filter is integrated in the housing of the treatment device.

7. The system according to claim 1 further comprising connecting channels for the pressure sensors, said connecting channels ending at sites in the treatment device and the means for creating a second flow resistance.

8. The system according to claim 7 whereby the treatment device comprises a housing and the connecting channels for the pressure sensors are run in the housing of the treatment device to a common connecting unit.

9. The system according to claim 8 wherein the ventilation tube system comprises a separate inhalation tube and exhalation tube whose junction is directly before the treatment device.

10. The system according to claim 9 wherein the separate inhalation tube and exhalation tube are coaxial.

11. The system according to claim 9 further comprising measuring tubes joined to the pressure sensors, a first connection connecting the junction to the treatment device, and a second connection connecting the measuring tubes to the common connecting unit, said first and second connections forming separate plug connections or a common plug connection, said measuring tubes running along the ventilation tube system or being integrated in the ventilation tube system.

12. A process for monitoring a ventilation system comprising a ventilation tubing system comprising a treatment device for creating a first flow resistance and a device selected from the group consisting of a filter and a heat and moisture exchanger, which comprises;
    (a) providing a monitor for evaluating ventilation system quantities selected from the group consisting of pressure quantities and flow quantities;
    (b) making a first pressure measurement by taking steps selected from the group consisting of (i) taking first and second pressure readings respectively upstream and downstream of the first flow resistance and (ii) taking a first differential pressure reading across the first flow resistance;
    (c) creating a second flow resistance suitable as a reference;
    (d) making a second pressure measurement for use as a reference by taking steps selected from the group consisting of (i) taking third and fourth pressure readings respectively upstream and downstream of the second flow resistance and (ii) taking a second differential pressure reading across the second flow resistance;
    (e) calculating selected parameters derived from the first and second pressure measurements as a function of time to determine the degree of permeability of the filter or exchanger; and
    (f) taking a step selected from the group consisting of (i) displaying the selected parameters; (ii) storing the selected parameters; and (iii) comparing the selected parameters with predetermined thresholds and determining whether to trigger an alarm based on the comparison.

13. The process according to claim 12 whereby one or more of the following selected parameters are calculated:

Flow resistance in the treatment device, tidal volumes, respiratory minute volume, breathing frequency, tube clogging, air trapping, i.e., captured air e.g. in asthmatics, respiratory passage pressure or the density of the respiratory system.

14. The process according to claim 12 whereby the reference flow resistance is created by an element selected from the group consisting of a section of the ventilation tubing system, a diaphragm and a filter.

15. The process according to claim 12 whereby the second pressure measurement is taken at sites in the treatment device and the means for creating a second flow resistance.

* * * * *

UNITED STATES PATENT AND TRADEMARK OFFICE
CERTIFICATE OF CORRECTION

PATENT NO.    : 6,308,706 B1
DATED         : October 30, 2001
INVENTOR(S)   : Léon Lammers et al.

It is certified that error appears in the above-identified patent and that said Letters Patent is hereby corrected as shown below:

<u>Title page,</u>
Item [30], the Foreign Priority Data correctly should read:

-- Mar. 8, 1996     (CH)........................607/96 --.

Signed and Sealed this

Twentieth Day of August, 2002

Attest:

Attesting Officer

JAMES E. ROGAN
*Director of the United States Patent and Trademark Office*